United States Patent [19]

Lentz et al.

[11] Patent Number: 4,564,701

[45] Date of Patent: Jan. 14, 1986

[54] CARBONYLATION PROCESS FOR THE PRODUCTION OF AROMATIC ACIDS

[75] Inventors: Carl M. Lentz, Mt. Carmel; James R. Overton; David D. Cornell, both of Kingsport, all of Tenn.

[73] Assignee: Eastman Kodak Company, Rochester, N.Y.

[21] Appl. No.: 693,488

[22] Filed: Jan. 22, 1985

[51] Int. Cl.$^4$ .................. C07C 51/10; C07C 51/14
[52] U.S. Cl. .................. 562/406; 546/327; 548/532; 549/71
[58] Field of Search .................. 562/406; 546/327; 548/532; 549/71

[56] References Cited

U.S. PATENT DOCUMENTS 3,501,518  3/1970  von Kutepow et al. .......... 562/406

*Primary Examiner*—Paul J. Killos
*Attorney, Agent, or Firm*—Clyde L. Tootle; J. Frederick Thomsen

[57] ABSTRACT

The present invention provides a process for the preparation of aryl carboxylic acids by the carbonylation of diaryliodonium salts. The diaryliodonium salts are reacted with carbon monoxide in the presence of a zero-valent palladium in a hydrocarbon acid reaction medium to prepare the aromatic carboxylic acids.

11 Claims, No Drawings

CARBONYLATION PROCESS FOR THE PRODUCTION OF AROMATIC ACIDS

DESCRIPTION

This invention relates to a novel catalytic carbonylation process for the production of aromatic acids. More particularly, this invention relates to a novel process for the carbonylation of diaryliodonium salts to form aromatic acids. The diaryliodonium salts are reacted with carbon monoxide in the presence of a zero valence palladium catalyst in a hydrocarbon acid reaction medium to prepare the aromatic carboxylic acids.

The preparation of carboxylic acid derivatives by carbonylation of aromatic halides catalyzed by Group VIIIA metal compounds is well known in the art. One such process is described in U.S. Pat. No. 2,640,071 whereby carboxylic acid derivatives are obtained from aryl halides using nickel complexes as catalyst using high reaction temperatures of 250°–450° C. and pressure of 300 to 1,000 atmospheres. A typical example is the conversion of p-dichlorobenzene to dialkyl terephthalate at 345° C. and 350 atmospheres of carbon monoxide in the presence of a catalytic amount of nickel.

Another carbonylation process discloses that diaryliodonium salts can be carbonylated to aromatic acid derivatives by reacting the diaryliodonium salt with carbon monoxide and an alcohol in the presence of a base and a palladium catalyst. See, for example, Nippon Kagaku Kaishi, 1982, No. 2, pp. 236. The carbonylation reaction is described by this reference as producing an aromatic ester or amide and an aryl iodide (specifically, iodobenzene). However, the reference implicitly discloses that the aryl iodide by-product is also carbonylated. Therefore, both the diphenyliodonium bromide and the iodobenzene by-product are reacted in the Kaishi process in the formation of the methyl benzoate product. The reaction of the iodobenzene by-product is undesirable in that an otherwise recyclable by-product is at least partially consumed in the reaction. As a result, additional quantities of the appropriate (and relatively expensive) aryl iodide must be provided to the reaction system.

It would therefore be an advance in the state of the art to provide a process for the selective carbonylation of particular aromatic halides to prepare aromatic acids under milder reaction conditions using less expensive reactants.

In accordance with the present invention, it has now been found that diaryliodonium salts can be carbonylated to the desired aromatic acids in the presence of a zero valence palladium in a hydrocarbon acid reaction medium. The carbonylation reaction specifically and selectively carbonylates the diaryliodonium salt and does not carbonylate the aromatic iodide present in the acidic reaction medium. This aromatic iodide recyclable by-product can then be used for the regeneration of the diaryliodonium starting material in the same acidic medium to provide a more efficient and inexpensive process.

The diaryliodonium salt employed as a starting material in the process of the present invention has the following chemical formula:

In the above Formula I, Ar and Ar' each independently represents a carbocyclic or heterocyclic aromatic moiety having about 5 to about 20 atoms in the ring or rings thereof. Such moieties can be derived from, for example, toluene, benzene, naphthalene, pyridine, thiophene, pyrrole, etc. Preferably, Ar and Ar' in the above formula represent the same aromatic moiety.

Moreover, the aryl groups of the diaryliodonium salt can be connected by means of a carbon or heteroatom bridge, as exemplified by the following formulas:

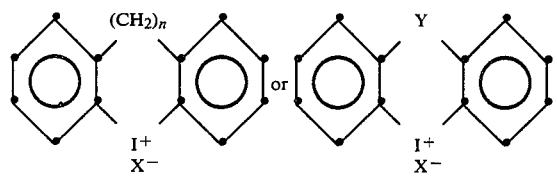

In the above formulas, n can equal 1, 2 or 3, and Y can represent O, S, or N.

The aromatic moieties of the diaryliodonium salt can be substituted or unsubstituted. When substituted, typical substituents include the halides, alkyl groups having up to about 12 carbon atoms, vinyl groups, carboxylic acid groups, carboxylic ester groups, ether groups, and the like.

In the above Formula I, X represents a weak acid anion. Preferred examples of such anions include acetate, trihaloacetate (e.g., trifluoroacetate), p-toluenesulfonate, benzenesulfonate, boron tetrafluoride, and the like.

Thus, preferred examples of the diaryliodonium salt include diphenyliodonium acetate, ditolyliodonium acetate, ditolyliodonium trifluoroacetate, diphenyliodonium tetrafluoroborate, diphenyliodonium p-toluenesulfonate, and the like.

The diaryliodonium salts employed in the process of the present invention can be prepared by the methods described by Beringer et al in *J.A.C.S.*, 81, 342 (1959), the disclosure of which is incorporated herein by reference in its entirety.

In the process of this invention, the diaryliodonium salt described above is reacted in a hydrocarbon acid solvent, such as acetic acid, butyric acid, propionic acid and the like. A stronger organic or inorganic acid may also be added to the hydrocarbon acid solvent in an amount of 0 percent to 15 percent, by weight, preferably 2 percent to 7 percent. Examples of such stronger acids are hexafluorophosphoric acid, p-toluenesulfonic acid, sulfuric acid, hexafluoroarsenic acid, trifluoroacetic acid, fluoroboric acid, 3,3,3-trifluoropropionic acid, hydrofluoric acid, fluorosulfuric acid, dichloroacetic acid and the like.

The zero-valent palladium catalyst is provided to the reaction system in the zero-valent form such, for example, preferably as the zero-valent metal supported on a suitable carrier or support material. For example, a highly desirable catalyst comprises 5%, by weight, palladium on a carbon support. The catalyst may also be provided in a form which there is an in situ formation to the zero-valent form, such as by the use of palladium acetate. The catalyst is present in a concentration of at least about 0.01 millimole per mole of iodonium salt, preferably, about 0.1 to 1 millimole per mole.

The catalytic carbonylation reaction of the present invention is conducted in the presence of carbon monoxide, which is employed in amounts such that the total reaction pressure is in the range of about 100 to about 500 psig. Superatmospheric pressure may be advantageous when a volatile reactant is employed or when an increase in the rate of reaction is desirable. Thus, reaction pressures from 100 psig to about 500 psig (about 700 kPa to about 3500 kPa) are suitable, with pressures from 100 psig up to about 250 psig (about 700 kPa to about 1750 kPa) being preferred.

The process of the present invention can be conducted at temperatures of about 50° C. to about 150° C., preferably about 80° C. to 130° C.

The reaction is carried out at a pH of less than about 5. The reaction under such acidic conditions prevents the carbonylation of the aryl iodide.

The aromatic carboxylic acid and catalyst can be removed from the reaction mixture by filtration. The aryl iodide by product as well as the hydrocarbon acid solvent system can be recycled to prepare the diaryliodonium salt. In contrast to prior art processes, the aryl iodide in the present process is not consumed (i.e., carbonylated to an aromatic acid or derivative thereof) and is therefore available for use in the preparation of the diaryliodonium salt starting material. This improvement represents a more efficient and cost effective process in that the iodide-containing product is preserved and recycled. In this manner, this relatively expensive component of the reaction system need not be supplied to the reaction process in considerable quantities on a continuous basis, as was necessary with prior art processes.

The novel process of the present invention therefore provides products which are useful as intermediates in the synthesis of polyesters (such as polyethylene terephthalate) and other useful polymeric materials in a unique and efficient manner.

The invention will be further illustrated by the following Examples although it will be understood that these Examples are included merely for purposes of illustration and are not intended to limit the scope of the invention.

EXAMPLES 1-10

The following Examples illustrate the carbonylation of a ditolyliodonium salt in the presence of a zero-valent palladium catalyst, a hydrocarbon acid solvent with a stronger acid and carbon monoxide to produce the corresponding p-toluic acid. The particular anion, catalyst, and acid employed in each example are indicated below in Table I. The catalyst was employed in a concentration of 0.05 millimole per mole of iodonium salt. The stronger acid was present in a concentration based on the weight percent of the acetic acid solvent present.

In each Example, into a laboratory autoclave was added 10.0 millimoles of the indicated diaryliodonium salt, 0.10 g of the indicated catalyst, the indicated weight percent stronger acid, and 100 ml of acetic acid. While carbon monoxide was fed beneath the surface of the reaction mixture at the indicated total pressure, the reaction mixture was heated to the indicated temperature and was held at that temperature for the indicated period of time. The resulting mixture was filtered hot to remove the catalyst and then cooled to 15° to 20° C. and filtered to remove the aryl carboxylic acid. The filtrate can then be used for recycling back to the preparation of the iodonium salt reaction. The aryl carboxylic acid product was washed with water and dried.

The results of these Examples are given below in Table I.

TABLE I

| Ex. | X | Acid | Catalyst | Temperature (°C.) | Pressure (psig) | Conversion (%) | Time (hrs) |
|---|---|---|---|---|---|---|---|
| 1 | OAc$^-$ | 3% H$_2$SO$_4$ | 5% Pd/C | 120 | 100 | 74.7 | 3 |
| 2 | OAc$^-$ | 5% HBF$_4$ | 5% Pd/C | 120 | 100 | 100 | 2 |
| 3 | OAc$^-$ | 10% HBF$_4$ | 5% Pd/C | 120 | 100 | 100 | 2 |
| 4 | OAc$^-$ | 3% H$_2$SO$_4$ 2% HF | 5% Pd/C | 120 | 100 | 44.5 | 3 |
| 5 | OAc$^-$ | 5% HPF$_6$ | 6 mesh Pd/C | 120 | 100 | 100 | 2 |
| 6 | OAc$^-$ | 5% HBF$_4$ | Pd/Al$_2$O$_3$ | 120 | 100 | 68 | 2 |
| 7 | BF$_4^-$ | 5% HBF$_4$ | 5% Pd/C | 100 | 100 | 80 | 2 |
| 8 | BF$_4^-$ | 5% HBF$_4$ | 5% Pd/C | 120 | 100 | 67 | 2 |
| 9 | HSO$_4^-$ | 5% H$_2$SO$_4$ | 5% Pd/C | 130 | 100 | 72 | 3 |
| 10 | —OCCF$_3$ (O=) | 5% HBF$_4$ | 5% Pd/C | 120 | 100 | 92 | 2 |
| 11 | OAC$^-$ | 3% H$_2$SO$_4$ | 5% Pd/C | 120 | 300 | 80 | 3 |

COMPARATIVE EXAMPLES 11-13

These Comparative Examples demonstrate the advantages of the present invention. In particular, these Compartive Examples demonstrate that the p-iodotoluene by-product of the above Examples is not carbonylated in the presence of a palladium catalyst, but is preserved for recycling.

About 10.0 millimoles p-iodotoluene was placed into a laboratory autoclave with the same amount catalyst and acetic acid used in the preceding Examples. The amount of stronger acid added is indicated. While carbon monoxide was fed beneath the surface of the reaction mixture at the indicated pressure, the reaction mixture was heated to the indicated temperature and was held at that temperature for the indicated period of time. Upon completion of reaction, the reaction mixture was worked up as described above. The results are given below in Table II.

TABLE II

| Comp. Ex. | Acid | Catalyst | Temperature (°C.) | Pressure (psig) | Conversion (%) | Time (hrs) |
|---|---|---|---|---|---|---|
| 11 | 3% H$_2$SO$_4$ | 5% Pd/C | 120 | 100 | 0 | 6 |
| 12 | 3% HBF$_4$ | 5% Pd/C | 120 | 100 | 0 | 6 |
| 13 | 3% HBF$_4$ | 5% Pd/C[1] | 150 | 300 | 0 | 6 |

These results clearly demonstrate that conversion of the p-iodotoluene substrate to the corresponding organic acid did not occur. Thus, in the overall process of the present invention, the p-iodotoluene by-product is not consumed but is available to be recycled, thereby enhancing the economics of the reaction.

The invention has been described in detail with particular reference to preferred embodiments thereof, but it will be understood that variations and modification can be effected within the spirit and scope of the invention.

We claim:

1. A process for the preparation of aromatic organic acid compounds of the formula $$ArCOH,$$
$$\overset{O}{\underset{\|}{}}$$

which comprises reacting a diaryliodonium salt of the formula

wherein Ar and Ar' each independently represents a carbocyclic or heterocyclic aromatic moiety having about 5 to about 20 atoms in the ring or rings thereof and X represents a weak acid anion, with carbon monoxide in the presence of a zero-valent palladium catalyst in a hydrocarbon acid reaction medium.

2. The process of claim 1 wherein Ar and Ar' are the same aromatic moiety.

3. The process of claim 2 wherein Ar and Ar' represent moieties derived from toluene, benzene, naphthalene, pyridine, thiophene, or pyrrole.

4. The process of claim 3 wherein X$^-$ represents acetate, trihaloacetate, p-toluenesulfonate, benzenesulfonate, hydroxide, iodide, bromide, or boron tetrafluoride.

5. The process of claim 4 wherein said hydrocarbon acid reaction medium comprises a member of the group consisting of acetic acid, butyric acid and propionic acid.

6. The process of claim 5 wherein the reaction temperature is about 50° to 150° C.

7. A process for the preparation of aromatic organic acid compounds of the formula

which comprises reacting a diaryliodonium salt of the formula

wherein Ar represents a moiety derived from toluene, benzene, naphthalene, pyridine, thiophene, or pyrrole and X represents a weak acid anion comprising acetate, trihaloacetate, p-toluenesulfonate, benzenesulfonate, hydroxide, iodide, bromide, or boron tetrafluoride, with carbon monoxide in the presence of a zero-valent palladium catalyst in a hydrocarbon acid reaction medium.

8. The process of claim 7 wherein Ar and Ar' are the same aromatic moiety.

9. The process of claim 8 wherein Ar represents a moiety derived from toluene or benzene.

10. The process of claim 9 wherein said hydrocarbon acid reaction medium comprises a member of the group consisting of acetic acid, butyric acid and propionic acid.

11. The process of claim 10 wherein the reaction temperature is about 80° to 130° C.

* * * * *